US012089956B2

United States Patent
Jiao

(10) Patent No.: US 12,089,956 B2
(45) Date of Patent: Sep. 17, 2024

(54) SIGNAL ACQUISITION SENSOR ARRAY, ELECTRONIC DEVICE, AND MATTRESS

(71) Applicant: BEIJING MICROVIBRATION DATANET TECHNOLOGY CO., LTD, Beijing (CN)

(72) Inventor: Xu Jiao, Beijing (CN)

(73) Assignee: BEIJING MICROVIBRATION DATANET TECHNOLOGY CO., LTD., Beijing (CN)

( * ) Notice: Subject to any disclaimer, the term of this patent is extended or adjusted under 35 U.S.C. 154(b) by 589 days.

(21) Appl. No.: 17/426,288

(22) PCT Filed: Mar. 11, 2019

(86) PCT No.: PCT/CN2019/077635
§ 371 (c)(1),
(2) Date: Jul. 28, 2021

(87) PCT Pub. No.: WO2020/181452
PCT Pub. Date: Sep. 17, 2020

(65) Prior Publication Data
US 2021/0386378 A1 Dec. 16, 2021

(51) Int. Cl.
*A61B 5/00* (2006.01)
*G01H 1/00* (2006.01)
(Continued)

(52) U.S. Cl.
CPC ............ *A61B 5/6892* (2013.01); *G01H 1/00* (2013.01); *G01H 1/06* (2013.01); *G01H 11/06* (2013.01);
(Continued)

(58) Field of Classification Search
CPC .. A61B 5/6892; A61B 2562/06; G01H 11/06; G01H 1/06; G01H 1/00; G01H 13/00; G01H 11/08
(Continued)

(56) References Cited

U.S. PATENT DOCUMENTS 5,505,072 A * 4/1996 Oreper ................... G01L 1/205
702/116
10,036,730 B2 * 7/2018 Wilkinson ......... G01N 29/2437
(Continued)

FOREIGN PATENT DOCUMENTS

CA 2556894 A1 * 9/2005 ............... A61G 7/05
CN 1951519 A * 4/2007
(Continued)

OTHER PUBLICATIONS

International Search Report issued on Oct. 30, 2019 in corresponding International Application No. PCT/CN2019/077635; 6 pages.

*Primary Examiner* — Stephanie E Bloss
*Assistant Examiner* — Kevin C Butler
(74) *Attorney, Agent, or Firm* — Maier & Maier, PLLC

(57) ABSTRACT

A signal acquisition sensor array, an electronic device, and a mattress. The sensor array includes: a connection layer, at least two types of sensor units, a signal acquisition circuit, and a signal line electrically connecting the sensor units with the signal acquisition circuit, where each of the sensor units includes: a first vibration-proof substrate, and a sensor element in one-to-one correspondence with the first vibration-proof substrate and is disposed between the first vibration-proof substrate and the connection layer; and the at least two types of sensor units are arranged in an array at intervals on the connection layer. The solution enables different physiological signals having widely different signal amplitudes to be all accurately detected by the sensor array.

13 Claims, 4 Drawing Sheets

(51) Int. Cl.
*G01H 1/06* (2006.01)
*G01H 11/06* (2006.01)
*G01H 11/08* (2006.01)
*G01H 13/00* (2006.01)

(52) U.S. Cl.
CPC ............. *G01H 11/08* (2013.01); *G01H 13/00* (2013.01); *A61B 2562/06* (2013.01)

(58) Field of Classification Search
USPC .......................................................... 73/651
See application file for complete search history.

(56) References Cited

U.S. PATENT DOCUMENTS

| | | | | |
|---|---|---|---|---|
| 2008/0109183 | A1* | 5/2008 | Shoureshi | G01K 1/026 374/E13.002 |
| 2012/0089033 | A1* | 4/2012 | Nemoto | A61B 5/0816 600/484 |
| 2015/0192548 | A1* | 7/2015 | Wilkinson | G01N 29/022 73/579 |
| 2021/0386378 | A1* | 12/2021 | Jiao | A61B 5/6892 |
| 2022/0273242 | A1* | 9/2022 | Jiao | A47C 27/053 |

FOREIGN PATENT DOCUMENTS

| | | | | |
|---|---|---|---|---|
| CN | 101201279 A | * | 6/2008 | |
| CN | 102631197 A | * | 8/2012 | |
| CN | 203988068 U | * | 12/2014 | |
| CN | 205211634 U | * | 5/2016 | |
| CN | 205607567 U | * | 9/2016 | |
| CN | 105997088 A | * | 10/2016 | ........... A61B 5/0816 |
| CN | 106419894 A | * | 2/2017 | .............. A61B 5/04 |
| CN | 106617907 A | * | 5/2017 | |
| CN | 106667435 A | * | 5/2017 | |
| CN | 106943258 A | * | 7/2017 | ........... A61B 5/6892 |
| CN | 206403512 U | * | 8/2017 | |
| CN | 107485229 A | * | 12/2017 | |
| CN | 206792383 A | | 12/2017 | |
| CN | 206792383 U | * | 12/2017 | |
| CN | 108158568 A | * | 6/2018 | ............ A61B 5/024 |
| CN | 108697245 A | | 10/2018 | |
| CN | 110087512 A | * | 8/2019 | ........... A61B 5/0205 |
| GB | 2547436 A | * | 8/2017 | ........... A61B 5/1036 |
| JP | 5519539 B2 | * | 6/2014 | ............. G06F 3/0233 |
| KR | 101715850 B1 | * | 3/2012 | ............. G06F 3/041 |
| WO | WO-2005011047 A2 | * | 2/2005 | .............. H01Q 21/06 |
| WO | WO-2015136486 A1 | * | 9/2015 | ............. A61B 5/447 |
| WO | WO-2017190085 A1 | * | 11/2017 | ......... A61B 5/02055 |

* cited by examiner

SIGNAL ACQUISITION SENSOR ARRAY, ELECTRONIC DEVICE, AND MATTRESS

TECHNICAL FIELD

The present application relates to the field of information technology, and particularly relates to a signal acquisition sensor array, an electronic device, and a mattress.

BACKGROUND

With the improvement of people's life quality, people are paying more and more attention to health. As the basis of health monitoring, some physiological signals such as body motion signals, breath signals and heartbeat signals need to be accurately acquired. In the prior art, there have already some devices for detecting these physiological signals, such as electronic bracelet and sphygmomanometer. However, on one hand, all these devices in the prior art can only detect one type of physiological signals, for example, the electronic bracelet can detect body motions or heartbeats, but the performance in breath detection of the electronic bracelet is unsatisfying; and the sphygmomanometer can detect heartbeats, but cannot detect body motions. On the other hand, the existing detection devices can only detect the parameters such as breath and heartbeats of users in a sitting, standing or moving state, the reference value of which is relatively low, so the reference value of signals detected by conventional detection devices in the prior art is also relatively low.

As an improvement, the solution of using a mattress with a sensor array has been provided. In this solution, a sensor array is used to detect body motion signals, breath signals and heartbeat signals. However, due to the fact that there is a great span of the signal amplitude of the same type of signals such as the body motion signals, the breath signals or the heartbeat signals and there may be a difference to several times or even to the magnitude order between different types of signals, it is difficult to detect all these signals accurately.

SUMMARY

To solve the above-mentioned problems, in a first aspect, one embodiment of the present application provides a signal acquisition sensor array, which comprises: a connection layer, at least two types of sensor units, a signal acquisition circuit, and a signal line electrically connecting the sensor units with the signal acquisition circuit, wherein each of the sensor units comprises: a first vibration-proof substrate; and a sensor element in one-to-one correspondence with the first vibration-proof substrate and is disposed between the first vibration-proof substrate and the connection layer; and the sensor elements of the at least two types of sensor units are arranged in an array at intervals on the connection layer.

Optionally, a plurality of the sensor units share the signal acquisition circuit.

Optionally, a product of a vibration-proof property of the first vibration-proof substrate of one sensor unit, a sensitivity of the sensor element of the one sensor unit and a sensitivity of the corresponding signal acquisition circuit is twice or more times of a product of a vibration-proof property of the first vibration-proof substrate of another sensor unit, a sensitivity of the sensor element of the other sensor unit and a sensitivity of the corresponding signal acquisition circuit.

Optionally, the signal acquisition sensor array comprises three types of sensor units, a product of a vibration-proof property of the first vibration-proof substrate of a first sensor unit of the three types of sensor units, a sensitivity of the sensor element of the first sensor unit and a sensitivity of the corresponding signal acquisition circuit is 2-20 times of a product of a vibration-proof property of the first vibration-proof substrate of a second sensor unit of the three types of sensor units, a sensitivity of the sensor element of the second sensor unit and the sensitivity of the corresponding signal acquisition circuit, and the product of the vibration-proof property of the first vibration-proof substrate of the second sensor unit, the sensitivity of the sensor element of the second sensor unit and the sensitivity of the corresponding signal acquisition circuit is 5-10 times of a product of a vibration-proof property of the first vibration-proof substrate of a third sensor unit of the three types of sensor units, the sensitivity of the sensor element of the third sensor unit and the sensitivity of the corresponding signal acquisition circuit.

Optionally, different types of sensor units correspond to a same signal acquisition circuit.

Optionally, the first vibration-proof substrate is made of a sponge with a pore characteristic parameter of 15 PPI-60 PPI.

Optionally, the connection layer is also used as a second vibration-proof substrate; or, each of the sensor units further comprises a second vibration-proof substrate separately disposed between the connection layer and the sensor element.

Optionally, where vibration-proof properties of the first vibration-proof substrates of the at least two types of sensor units are different, a vibration-proof property of the second vibration-proof substrate is between a maximum value and a minimum value of the vibration-proof properties of the at least two types of first vibration-proof substrates.

Optionally, the second vibration-proof substrate is made of a sponge with a pore characteristic parameter of 25 PPI-50 PPI.

Optionally, the length of the signal line is greater than a maximum extension length of the connection layer in an extension direction of the signal line between connection points at two ends of the signal line.

Optionally, the sampling frequency of the signal acquisition circuit is not less than 40 Hz.

Optionally, the signal acquisition circuit has different sampling frequencies for different sensor units.

In a second aspect, another embodiment of the present application provides an electronic device, which comprises a processor and the sensor array mentioned above.

In a third aspect, another embodiment of the present application provides a mattress, which comprises a body and the sensor array mentioned above.

In one or more embodiments of the present application, at least two types of sensor units are arranged in an array at intervals, and the sensor elements in the sensor units are in one-to-one correspondence with the first vibration-proof substrates and are disposed between the first vibration-proof substrates and the connection layer, such that different signals will be attenuated to different degrees when transmitted to the sensor units, and strong force coupling between the sensor units is eliminated, thus making different physiological signals having widely different signal amplitudes to be all accurately detected by the sensor array.

BRIEF DESCRIPTION OF THE DRAWINGS

To more clearly explain the technical solutions of the embodiments of the present application, the drawings used in the description of the embodiments of the present application or the prior art will be briefly introduced below. Obviously, the drawings in the following description only illustrate some embodiments of the present application. Those ordinarily skilled in the art can obtain other drawings according to the following ones without paying creative effort.

DETAILED DESCRIPTION OF EMBODIMENTS

The technical solutions of the embodiments of the present application will be clearly and completely described below in conjunction with the drawings of the embodiments of the present application. Obviously, the embodiments in the following description are merely illustrative ones, and are not all possible ones of the present application. All other embodiments obtained by those ordinarily skilled in the art without paying creative effort should also fall within the scope of the present application.

First all of, it should be pointed out that the inventor of the present application targeted, based on a great deal of experiments and data researches, the main reason why different physiological signals having widely different signal amplitudes cannot be all accurately detected by existing sensor arrays to the following contradiction: existing combinations of a sensor element, a signal acquisition circuit and a vibration-proof material cannot reconcile a span to the magnitude order of the amplitude and sufficient precision; and force coupling possibly existing between sensor units of a planar sensor array may lead to the propagation of signals, which changes point vibrations into planar signals. Based on the recognition on this reason, the inventor of the invention puts forwards the solutions of the following embodiments to solve the contradiction.

Embodiment 1

Figure 1:
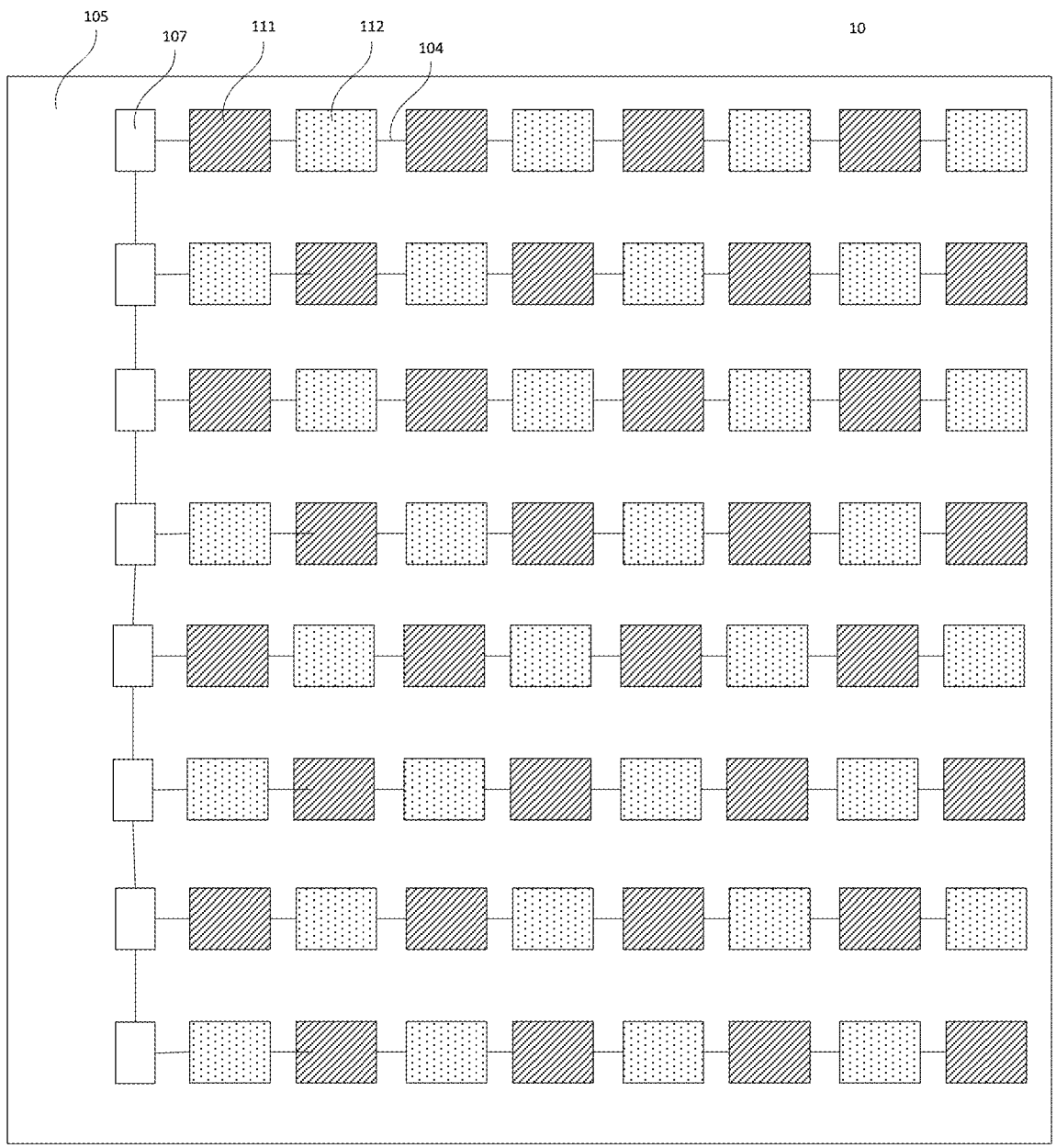
FIG. 1 is a top view of a signal acquisition sensor array according to one embodiment of the present application.
Figure 2:
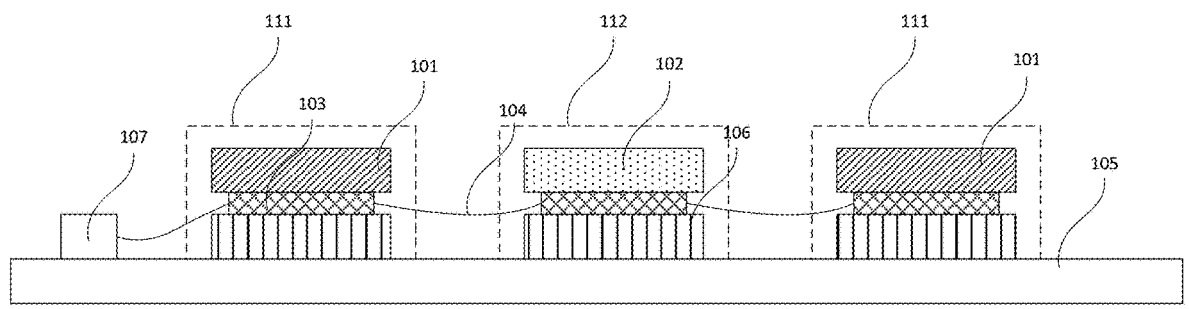
FIG. 2 is a sectional view of a signal acquisition sensor array according to one embodiment of the present application.

Referring to FIG. 1 and FIG. 2, this embodiment discloses a signal acquisition sensor array 10, which comprises: a connection layer 105, at least two types of sensor units 111 and 112, a signal acquisition circuit 107, and a signal line 104 for electrically connecting the sensor units 111 or 112 with the signal acquisition circuit 107, wherein each sensor unit 111 or 112 further comprises: a first vibration-proof substrate 101 or 102, and a sensor element 103 in one-to-one correspondence with the first vibration-proof substrate 101 or 102 and is disposed between the first vibration-proof substrate 101 or 102 and the connection layer 105; and the at least two types of sensor units are arranged in an array at intervals on the connection layer. The vibration-proof substrate refers to a material with a vibration resisting (attenuating) effect such as sponges, rubber and foam. The vibration-proof substrate may be a sheet, or a block with a concave portion. If the vibration-proof substrate is a block with a concave portion, the sensor element can be accommodated in the concave portion, and the vibration-proof effect can be further adjusted by adjusting the size of the concave portion. In FIG. 1 and FIG. 2, the signal line is successively connected in series between the sensor units. Those skilled in the art would appreciate that the signal line may also be connected between each sensor unit 111 or 112 with the signal acquisition circuit 107. At least two types of sensor units are arranged in an array at intervals, and the sensor element in each sensor unit is in one-to-one correspondence with the first vibration-proof substrate and is disposed between the first vibration-proof substrate and the connection layer, such that different signals will be attenuated to different degrees when transmitted to the sensor units; and the first vibration-proof substrates are separated, such that strong force coupling between the sensor units is eliminated, thus making different physiological signals having widely different signal amplitudes to be all accurately detected by the sensor array.

FIG. 1 illustrates an 8*8 array. Those skilled in the art would appreciate that the 8*8 array is merely illustrative, and the sensor units may also be combined in an array including other numbers of rows and columns.

Optically, a substrate layer 106 is further disposed between each sensor element 103 and the connection layer 105 and is used for supporting the sensor element and a related regulating circuit, such that the whole sensor array has a high rigidity and can be prevented from being damaged.

Figure 5:
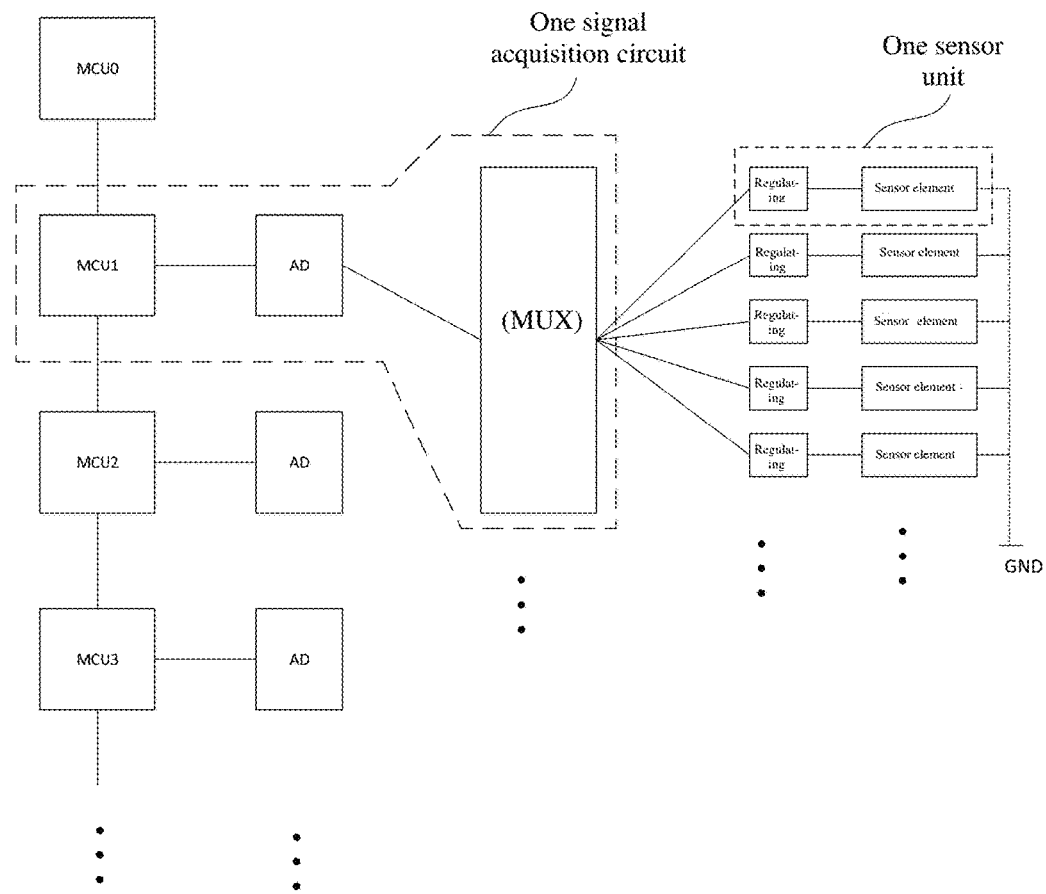
FIG. 5 is a schematic diagram of a signal processing circuit according to one embodiment of the present application.

Optionally, as shown in FIG. 5, a plurality of the sensor units 111 or 112 share one signal acquisition circuit 107, such that large-area acquisition can be realized by means of a few acquisition circuits, thus reducing costs; and the time interval of signal acquisition can be shortened through a series bus or other techniques, thus increasing the signal acquisition rate. Similarly, at least one signal acquisition circuit 107 is further connected to a central processing unit of the whole array.

Optically, the product of the vibration-proof property of the first vibration-proof substrate of the sensor unit 111, the sensitivity of the sensor element of the sensor unit 111 and the sensitivity of the corresponding signal acquisition circuit is twice or more times of the product of the vibration-proof property of the first vibration-proof substrate of the sensor unit 112, the sensitivity of the sensor element of the sensor unit 112 and the sensitivity of the corresponding signal acquisition circuit. Herein, the vibration-proof property refers to the vibration attenuation factor. For example, if the vibration-proof property of a material is 40%, it means that the material can attenuate the vibration by 40%, and only 60% of the vibration will be transmitted from one side to the other side of the material. The meaning of the sensitivity of the sensor and the meaning of the sensitivity of the acquisition circuit have been comprehensively defined in the prior art, and for the sake of brevity, will no longer be repeated.

The sensor element may be a piezoelectric patch, or one or a combination of several of, a strain gauge, a piezoresistive sensor, and etc. An operational amplifier circuit is disposed in the sensor element to amplify an initial signal. Different types of elements or different amplification factors of the operational amplifier circuit can be adopted to realize different sensitivities of the sensor element.

Figure 3:
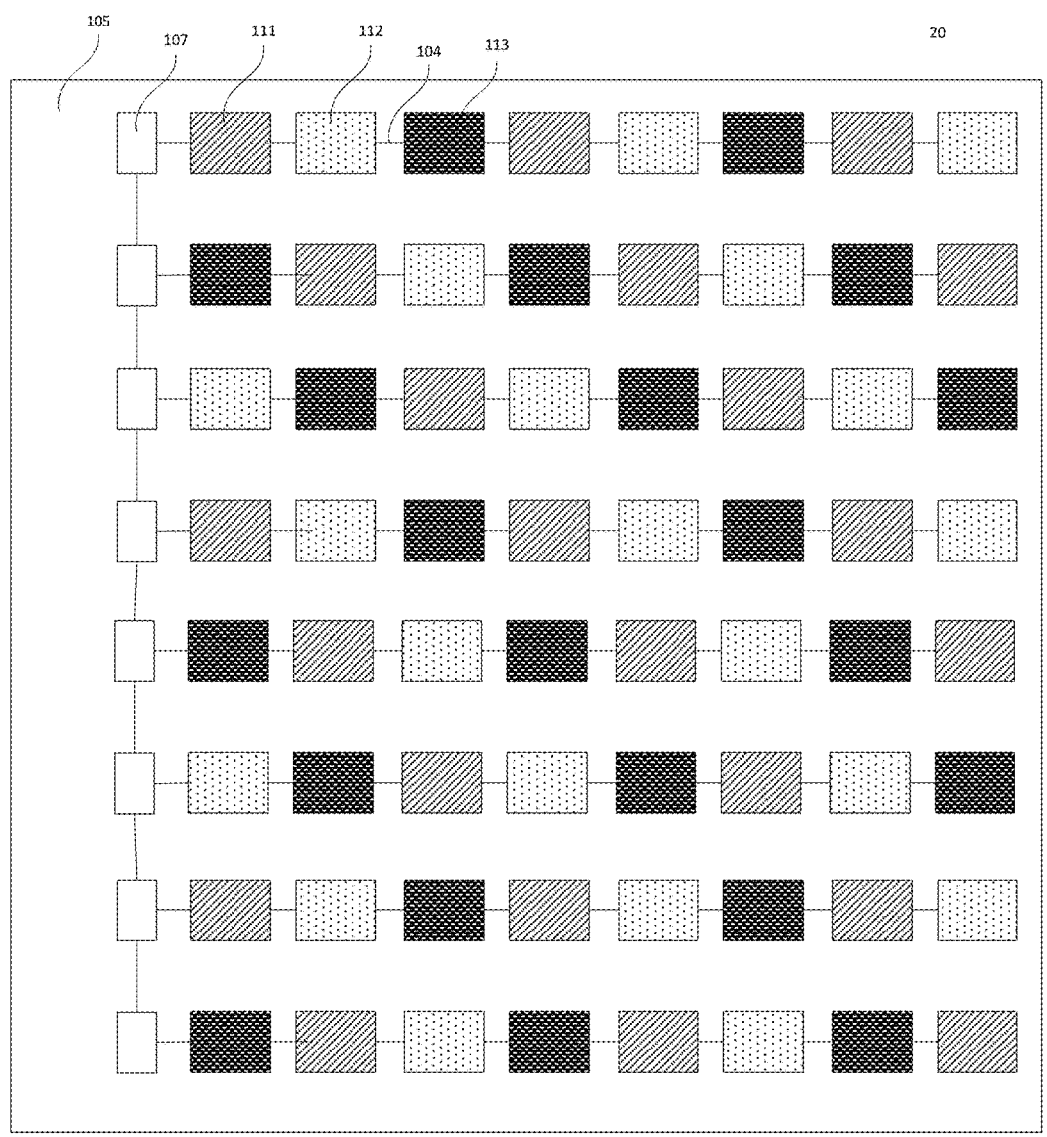
FIG. 3 is a top view of a signal acquisition sensor array according to another embodiment of the present application.

Optionally, as shown in FIG. 3, the signal acquisition sensor array 20 comprises three types of sensor units, wherein the product of the vibration-proof property of the first vibration-proof substrate of a first sensor unit 111, the sensitivity of the sensor element of the first sensor unit 111 and the sensitivity of the corresponding signal acquisition circuit is 2-20 times of the product of the vibration-proof property of the first vibration-proof substrate of a second sensor unit 112, the sensitivity of the sensor element of the second sensor unit 112 and the sensitivity of the corresponding signal acquisition circuit; and the product of the vibration-proof property of the first vibration-proof substrate of the second sensor unit 112, the sensitivity of the sensor element of the second sensor unit 112 and the sensitivity of the corresponding signal acquisition circuit is 5-10 times of the product of the vibration-proof property of the first vibration-proof substrate of a third sensor unit 113, the sensitivity of the sensor element of the third sensor unit 113 and the sensitivity of the corresponding signal acquisition circuit.

In addition, signals can be further classified, and other numbers of types of sensor units of can be adopted, correspondingly. For example, in case where signals are classified according to large-amplitude body motion, small-amplitude body motion, heartbeat, pulse and breath, five types of sensor units are adopted.

Optionally, "the product of the vibration-proof property of the first vibration-proof substrate of the sensor unit 111, the sensitivity of the sensor element of the sensor unit 111 and the sensitivity of the corresponding signal acquisition circuit is twice or more times of the product of the vibration-proof property of the first vibration-proof substrate of the sensor unit 112, the sensitivity of the sensor element of the sensor unit 112 and the sensitivity of the corresponding signal acquisition circuit" can be implemented in different manners. For example, if the first vibration-proof substrates of the two types of sensor units 111 and 112 are identical and the sensitivities of the corresponding signal acquisition circuit are also identical, the sensitivity of the sensor element of one sensor unit is twice or more times of the sensitivity of the sensor element of the other sensor unit. Or, if the sensitivities of the sensor elements are identical and the sensitivities of the corresponding signal acquisition circuit are also identical, the vibration-proof property of the first vibration-proof substrate of one sensor unit is twice or more times of the vibration-proof property of the first vibration-proof substrate of the other sensor unit. Or, if the first vibration-proof substrates of the two types of sensor units 111 and 112 are identical and the sensitivities of the sensor elements are also identical, the sensitivity of the signal acquisition circuit corresponding to one sensor unit is adjusted to be twice or more times of the sensitivity of the signal acquisition circuit corresponding to the other sensor unit, and although is not shown, those skilled in the art would appreciate that the two types of sensor units are connected to different signal acquisition circuits in this case. Preferably, different types of sensor units correspond to the same signal acquisition circuit, so as to lower the circuit design difficulty. The cases where one of the three parameters, namely the vibration-proof property, the sensitivity of the sensor unit and the sensitivity of the signal acquisition circuit varies and the other two parameters are identical have been illustrated above by way of examples, but it is also feasible to keep one parameter identical and change the other two parameters, or to change all these three parameters. However, the debugging difficulty will become higher with the increase of the number of variable parameters.

Optionally, the first vibration-proof substrate 101 or 102 is made of a sponge with a pore characteristic parameter of 15 PPI-60 PPI. Preferably, the first vibration-proof substrate 101 or 102 is made of a sponge with a pore characteristic parameter of 20 PPI-50 PPI. It should be explained herein that the application of the sponge is determined according to the indicator "PPI", which refers to the par per inch. The higher the PPI, the softer the sponge; the lower the PPI, the harder the sponge. The sponge is cellular. Cells can be seen when the sponge is observed with a microscope. The larger the cells are, the lower the PPI is, and the harder the sponge (the smaller the par per inch) is.

Figure 4:
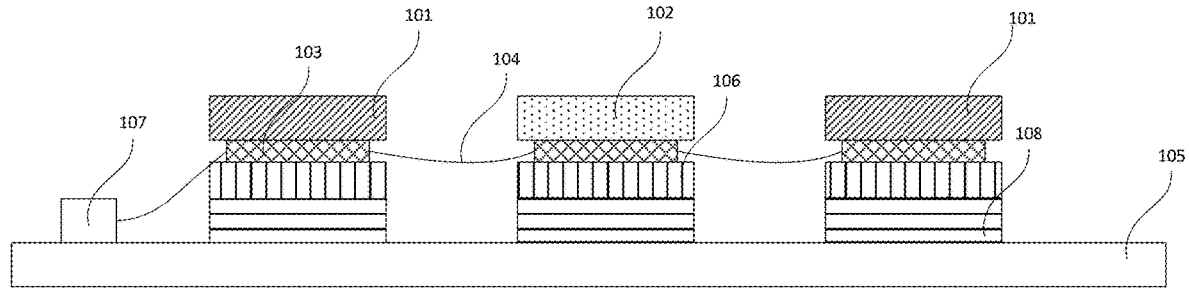
FIG. 4 is a sectional view of a signal acquisition sensor array according to another embodiment of the present application.

Optionally, as shown in FIG. 2, the connecting layer 105 is also used as a second vibration-proof substrate. As a substation, as shown in FIG. 4, each sensor unit further comprises a second vibration-proof substrate 108 separately disposed between the connection layer 105 and the sensor element. When the sensor array is provided with a substrate layer 106, the second vibration-proof substrate 108 is preferably arranged between the substrate layer 106 and the connection layer 105.

Optionally, the second vibration-proof substrate is made of a sponge with a pore characteristic parameter of 25 PPI-50 PPI. Preferably, the second vibration-proof substrate is made of a sponge with a pore characteristic parameter of 30 PPI-40 PPI.

Optionally, in the case where the vibration-proof properties of the first vibration-proof substrates of the at least two types of sensor units are different, the vibration-proof property of the second vibration-proof substrate is between a maximum value and a minimum value of the vibration-proof properties of the at least two vibration-proof substrates, which can be implemented by adopting different vibration-proof substrates. For example, the first vibration-proof substrate 101 is made of a sponge with a pore characteristic parameter of 25 PPI, the first vibration-proof substrate 102 is made of a sponge with a pore characteristic parameter of 50 PPI, and the second vibration-proof substrate is made of a sponge with a pore characteristic parameter of 35 PPI.

Optionally, the length of the signal line is greater than a maximum extension length of the connection layer in the extension direction of the signal line between connection points at two ends of the signal line. When the signal line is connected in series between sensor units, the two connection points at the two ends of the signal line are welding points between two sensor units and the signal line. When the signal line is connected between a sensor units and a signal acquisition circuit, the connection points at the two ends of the signal line are welding points between the sensor unit and the signal line and between the signal acquisition circuit and the signal line. By setting the length of the signal line greater than the maximum extension length in the extension direction of the signal line of the connection layer between the connection points at the two ends of the signal line, breakage of the signal line will not be caused by space changes between the sensor units, and the reliability of the sensor array is higher.

Optionally, the sampling frequency of the signal acquisition circuit is not less than 40 Hz. Preferably, the sampling frequency of the signal acquisition circuit is not less than 100 Hz. When the sampling frequency of the signal acquisition circuit is not less than 100 Hz, it not only can acquire body motion signals, breath signals and heartbeat signals, but also can recognize abnormal heartbeat. More preferably, the sampling frequency of the signal acquisition circuit is not less than 200 Hz. In this case, more scenes such as blood pressure, blood oxygen, the hardness of vessel walls, the degree of thrombus, and neurological problems can be recognized, and the reliability is further improved.

Herein, a signal processing circuit of the present application will be described with reference to the schematic diagram illustrated by FIG. 5. From the point of view of circuit, each sensor unit comprises a sensor element and a regulating circuit, wherein the sensor element is used for sensing the pressure generated by a human body, converting the pressure into an electric signal and outputting the electric signal to the regulating circuit, and the regulating circuit regulates the electric signal output by the sensor element by amplification and filtering and then outputs the regulated electric signal to the signal acquisition circuit. The signal acquisition circuit can acquire electric signals of a plurality of sensor units by means of a multiplexer circuit. A multiplexer is connected to an AD (analog-digital) sampling circuit, the AD sampling circuit samples an analog signal, converts the analog signal into a digital signal, and then outputs the digital signal to MCUs (micro control units). The MCUs (MCU0, MCU1, MCU2, MCU3, etc.) include a master MCU (MCU0 in FIG. 5) and slave MCUs (MCU1, MCU2, MCU3, etc. in FIG. 5). The slave MCUs are used for receiving an acquisition signal from the AD sampling circuit and controlling the parameters of the AD sampling circuit such as the sampling frequency and the sampling time. The master MCU is used for receiving signals from the slave MCUs, operating and outputting the signals, and controlling the slave MCUs. A plurality of sensor units share one AD sampling circuit, such that costs can be reduced. Preferably, the signal sampling circuit has different sampling frequencies for different sensor units. For example, the signal acquisition circuit may comprise a time reference module, a sampling time adjustment module, a sampling frequency adjustment module and other sub-modules, so as to realize different AD sampling frequencies and times. By setting AD sampling frequencies and times, the AD sampling circuit can be controlled to acquire signals of different sensor units in a time-division and variable-frequency (at different frequencies) manner, and sensor units relating to weak signals can be densely sampled, As a result, the sampling range in frequency domain is widened, and channels and data processing and storage resources are saved. By configuring the MCUs, the sampling frequency of any sensor unit can be adjusted within 10-20 kHz, wherein heart sound signals and pulmonary sound signals can be acquired by a high frequency. By means of synchronous control of the master MCU, the whole sensor array can realize flexible sampling within a wide signal frequency domain of 0.1 Hz-10 kHz. Meanwhile, by adopting variable-frequency sampling for different sensor units, the application of algorithms such as energy statistics or signal mode matching is made possible, and a most effective position and a most effective bandwidth can be selected to realize the detection of physical signs such as heart sounds and pulmonary sounds without the disturbance of large signals such as body motion signals.

Figure 6:
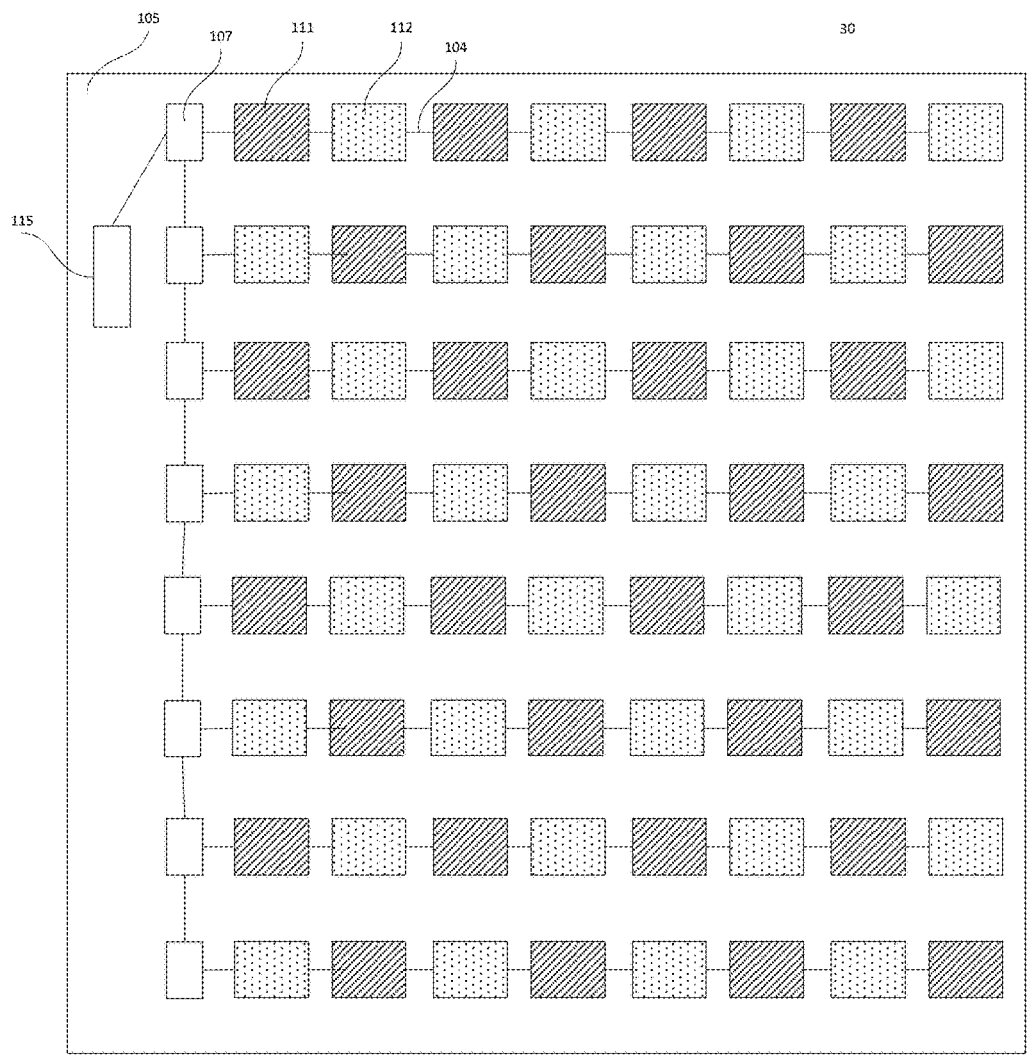
FIG. 6 is a schematic diagram of an electronic device of the present application.

Correspondingly, as shown in FIG. 6, the present application further discloses an electronic device 30, which comprises a processor 115 and any one sensor array mentioned above.

Figure 7:
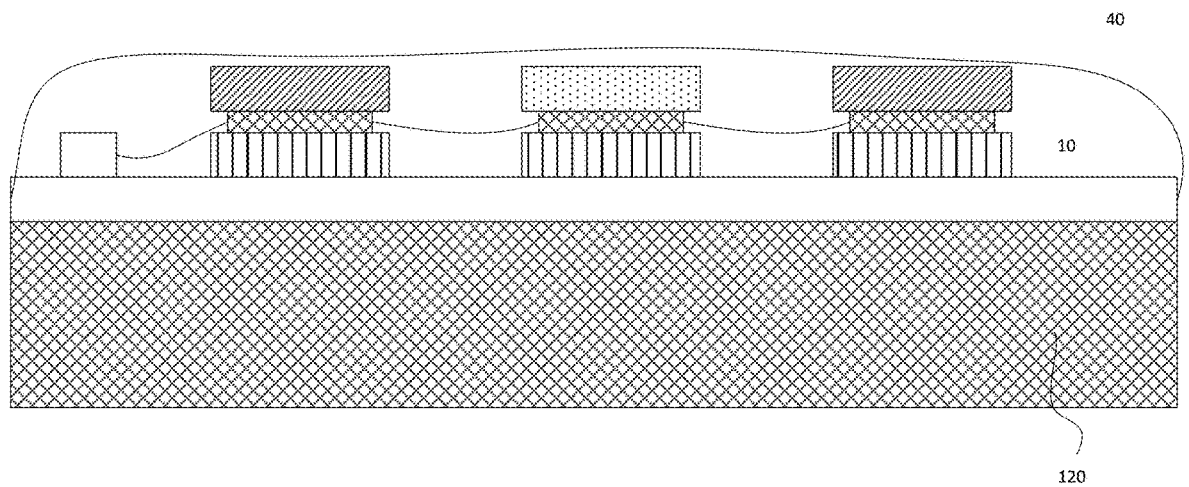
FIG. 7 is a schematic diagram of a mattress according to one embodiment of the present application.

Correspondingly, as shown in FIG. 7, the present application further discloses a mattress 40, which comprises a mattress body 120 and any one sensor array mentioned above. The mattress body may further comprise a cushion and a cover over the cushion. The design of the mattress belongs to the prior art, and will no longer be detailed herein.

The signal acquisition sensor array, the electronic device and the mattress provided by the present application have been introduced in detail above. In this specification, the principle and implementations of the present invention are expounded with reference to specific embodiments, but the description of the above embodiments is merely for assisting in understanding the method and core concept of the present application. Based on the concept of the present application, those ordinarily skilled in the art can make different variations and improvements, which all should also fall within the scope defined by the claims of the present application.

What is claimed is:

1. A signal acquisition sensor array, comprising: a connection layer, at least two types of sensor units, a signal acquisition circuit, and a signal line electrically connecting the sensor units with the signal acquisition circuit, wherein each of the at least two types of sensor units comprises:
 a first vibration-proof substrate; and
 a sensor element in one-to-one correspondence with the first vibration-proof substrate, is the sensor element disposed between the first vibration-proof substrate and the connection layer;
 wherein the at least two types of sensor units are arranged in an array at intervals on the connection layer;
 wherein a product of a vibration-proof property of the first vibration-proof substrate of one sensor unit, a sensitivity of the sensor element of the one sensor unit and a sensitivity of the corresponding signal acquisition circuit is twice or more times of a product of a vibration-proof property of the first vibration-proof substrate of another sensor unit, a sensitivity of the sensor element of the other sensor unit and a sensitivity of the corresponding signal acquisition circuit.

2. The signal acquisition sensor array according to claim 1, wherein a plurality of the at least two types of sensor units share the signal acquisition circuit.

3. The signal acquisition sensor array according to claim 1, wherein
 the signal acquisition sensor array comprises three types of sensor units,
 a product of a vibration-proof property of the first vibration-proof substrate of a first sensor unit of the three types of sensor units, a sensitivity of the sensor element of the first sensor unit and a sensitivity of the corresponding signal acquisition circuit is 2-20 times of a product of a vibration-proof property of the first vibration-proof substrate of a second sensor unit of the three types of sensor units, a sensitivity of the sensor element of the second sensor unit and the sensitivity of the corresponding signal acquisition circuit, and
 the product of the vibration-proof property of the first vibration-proof substrate of the second sensor unit, the sensitivity of the sensor element of the second sensor unit and the sensitivity of the corresponding signal acquisition circuit is 5-10 times of a product of a vibration-proof property of the first vibration-proof substrate of a third sensor unit of the three types of sensor units, the sensitivity of the sensor element of the third sensor unit and the sensitivity of the corresponding signal acquisition circuit.

4. The signal acquisition sensor array according to claim 1, wherein different types of sensor units correspond to a same signal acquisition circuit.

5. The signal acquisition sensor array according to claim 1, wherein the first vibration-proof substrate is made of a sponge with a pore characteristic parameter of 15 PPI-60 PPI.

6. The signal acquisition sensor array according to claim 1, wherein
 the connection layer is also used as a second vibration-proof substrate; or each of the at least two types of sensor units further comprises a second vibration-proof substrate separately disposed between the connection layer and the sensor element.

7. The signal acquisition sensor array according to claim 6, wherein
where vibration-proof properties of the first vibration-proof substrates of the at least two types of sensor units are different, a vibration-proof property of the second vibration-proof substrate is between a maximum value and a minimum value of the vibration-proof properties of the at least two types of first vibration-proof substrates.

8. The signal acquisition sensor array according to claim 6, wherein the second vibration-proof substrate is made of a sponge with a pore characteristic parameter of 25 PPI-50 PPI.

9. The signal acquisition sensor array according to claim 1, wherein a length of the signal line is greater than a maximum extension length of the connection layer in an extension direction of the signal line between connection points at two ends of the signal line.

10. The signal acquisition sensor array according to claim 1, wherein a sampling frequency of the signal acquisition circuit is not less than 40 Hz.

11. The signal acquisition sensor array according to claim 1, wherein the signal acquisition circuit has different sampling frequencies for different sensor units.

12. An electronic device, comprising a processor and the signal acquisition sensor array according to claim 1.

13. A mattress, comprising a body and the signal acquisition sensor array according to claim 1.

* * * * *